United States Patent [19]

Sternstein

[11] 4,096,741

[45] Jun. 27, 1978

[54] MATERIALS TESTING DEVICE

[76] Inventor: Sanford S. Sternstein, 9 Oak Tree La., Schenectady, N.Y. 12309

[21] Appl. No.: 716,647

[22] Filed: Aug. 23, 1976

[51] Int. Cl.² .............................................. G01N 3/08
[52] U.S. Cl. ........................................ 73/90; 73/93
[58] Field of Search ...................... 73/90, 92, 93, 15.6, 73/89, 95

[56] References Cited

U.S. PATENT DOCUMENTS

| 3,374,665 | 3/1968 | Preston ..................................... 73/90 |
| 3,712,125 | 1/1973 | Meyer ...................................... 73/90 |
| 3,777,557 | 12/1973 | Dunlap et al. ........................ 73/90 X |
| 3,826,902 | 7/1974 | Claxton ................................. 73/95 X |

OTHER PUBLICATIONS

Kronick et al.–"Transducer for Studies of Active Muscle"–23rd ACEMB–Wash. D.C.–Nov. 15-19, 1970–p. 63.
"New Range of Materials Testers"–Elec. & Electron, M.F.R. (G.B.)–vol. 14, No. 12, Dec. 1970 — pp. 12 to 14.

*Primary Examiner*—Charles A. Ruehl
*Attorney, Agent, or Firm*—Rose & Edell

[57] ABSTRACT

The invention provides a d.c. motor and motor control circuit to conduct characterization tests on materials by applying constant loads to or affecting constant displacements of physical samples of various materials for transient tests purposes. The actuator, a voice coil motor, and a wave shaping input circuit in associated motor control circuitry provide stable, precise control of load during creep tests without backlash and stick slip and stable precise control of displacement during a relaxation test without dither thus providing rapid response whereby results may be obtained in milliseconds and further permitting the same equipment to be employed for dynamic tests. The motor is controlled by an underdamped servo loop which in turn receives a command signal from a filter circuit having a rise time optimized with respect to the mechanical constants of the system. In this manner the leading edge of an input step signal is delayed before being applied to the underdamped servo so as to avoid overshoot and yet reach maximum value in the shortest time possible for the overall system. A further feature of the present invention is an interlock arrangement which prevents calibration signals for a measured parameter from being applied to the system during a test in which that parameter is controlling closed loop servo loop operation.

12 Claims, 5 Drawing Figures

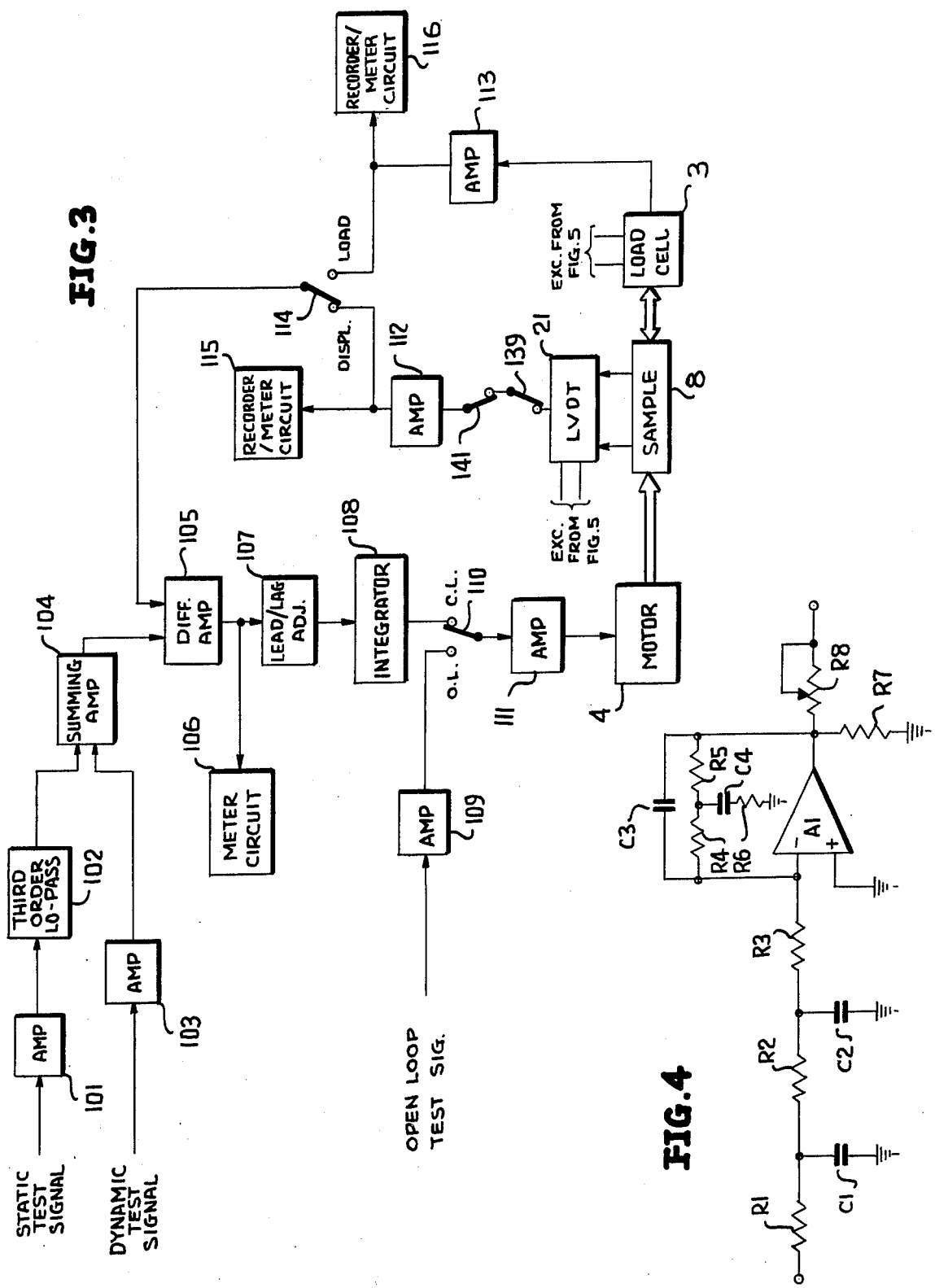

MATERIALS TESTING DEVICE

BACKGROUND OF THE INVENTION

The present invention relates to apparatus and associated circuitry for conducting transient characterization tests on materials and more particularly to apparatus which permits such tests to be conducted in 10 to 20 milliseconds.

It is conventional to define, i.e., characterize, materials by conducting various types of tests on samples of the material to be defined. The tests to which the present invention relates are non-destructive, transient, characterization tests relating to creep and relaxation properties of viscoelastic polymers and other materials. A creep test requires the application of a constant load and measurement of elongation while a stress relaxation test requires constant elongation and measurement of stress. These tests are conducted at low levels of physical parameters with loads of about ± 25 lbs. and elongations of about ± 10 mils.

Current equipment is such that transient characterization tests must be conducted over intervals of 1 second or more and more rapid testing is accomplished by dynamic testing at various frequencies. Current equipment limits transient testing to more than 1 second intervals due to poor rate of response of the transient testing equipment and the associated d.c. circuitry.

As to dynamic tests such tests are usually conducted by hydraulic systems where, due to O-rings and other static friction problems, dither must be employed. Testing at the low levels indicated, 10 mils elongation, 25 lbs. load, becomes difficult in such an environment. A further difficulty which is inherent in dynamic tests is that characterization is valid only if such tests are conducted at a number of different frequencies. Circuit complexity is also encountered due to the necessity of making highly accurate phase measurement tests.

It is an object of the present invention to provide an apparatus and associated circuit capable of conducting both transient and dynamic characterization tests on materials conducting transient tests at intervals as short as 10-20 milliseconds and dynamic responses to 200 Hz minimum.

It is another object of the present invention to provide apparatus for producing valid transient characterization test data of materials in short time intervals.

It is still another object of the present invention to provide a voice coil motor to employ both d.c. and a.c. motor characteristics to a materials testing apparatus whereby rapid response in both transient and dynamic modes of response can be provided in a single apparatus.

It is yet another object of the present invention to provide a voice coil motor and rapid processes in the input circuit to a control system whereby the electrical system and motor response of a testing apparatus may be tailored to mechanical response of the apparatus whereby overshoot and undershoot are substantially eliminated, i.e., error resulting from lost information due to such is less than the error resulting from temperature variations.

In prior art measurement systems of the type described there exists a problem related to calibration. In particular, if a calibrate signal for a specified parameter is applied to the system during a test mode when the parameter controls the servo loop, the calibrate signal introduces large transient conditions into the motor-controlling servo loop. Such transient conditions, at the very least, ruin any measurement being conducted; at worst, the transient can result in destruction of the test sample or the system itself. That is not to say that calibration can never be performed during measurement. For example, during open loop operation the problem does not exist. Further, when the closed loop is controlled by the sample displacement, a calibration can be performed without adverse consequences; likewise, when the loop is controlled by the applied load, displacement calibration presents no problem.

It is therefore another object of the present invention to provide an automatic interlock arrangement which prevents application of a calibration signal under conditions which could adversely affect the system.

SUMMARY OF THE INVENTION

The present invention utilizes a voice coil motor in a static test mode to impart the force, either tensile or compressive, to a specimen to be tested. Heretofore voice coil motors have only been used for dynamic testing. A load cell or linear variable differential transformer, depending on the test to be performed, applies a feedback signal to a motor control in a servo loop. The command signal for the loop is applied through an input circuit of a characteristic such that the first two derivatives of the input signal are suppressed such that the time of response of the input circuit is of the same order of magnitude as the mechanical system. Thus any components of the input signal due to transient response of the mechanical system are suppressed prior to application of the signal to the servo loop which can then be operated in the underdamped condition. This latter feature is of particular importance, since the use of the voice coil motor and other features, described below, of the design of the mechanical system which permit tests to be conducted in 10-20 milliseconds would otherwise produce oscillation of the system upon the application of rapidly rising signal to the voice coil motor. Such other features relate to the virtual direct coupling of the specimen of material to be tested to the motor and the load cell, the very low compliance of the load cell and the low inertia of the motor.

Another feature of the present invention is an automatic interlock arrangement which precludes application of a displacement calibration signal to the closed servo loop during the displacement control mode and precludes application of a load calibration signal to the closed servo loop during load control mode.

BRIEF DESCRIPTION OF THE DRAWINGS

The above and still further objects, features and advantages of the present invention will become apparent upon consideration of the following detailed description of one specific embodiment thereof, especially when taken in conjunction with the accompanying drawings, wherein:

FIG. 3 is a functional block diagram of the control circuitry employed to drive the motor in the arrangement of FIG. 1;

FIG. 4 is a schematic diagram of a filter circuit employed in the control circuitry of FIG. 3.

DESCRIPTION OF PREFERRED EMBODIMENTS

Figure 1:
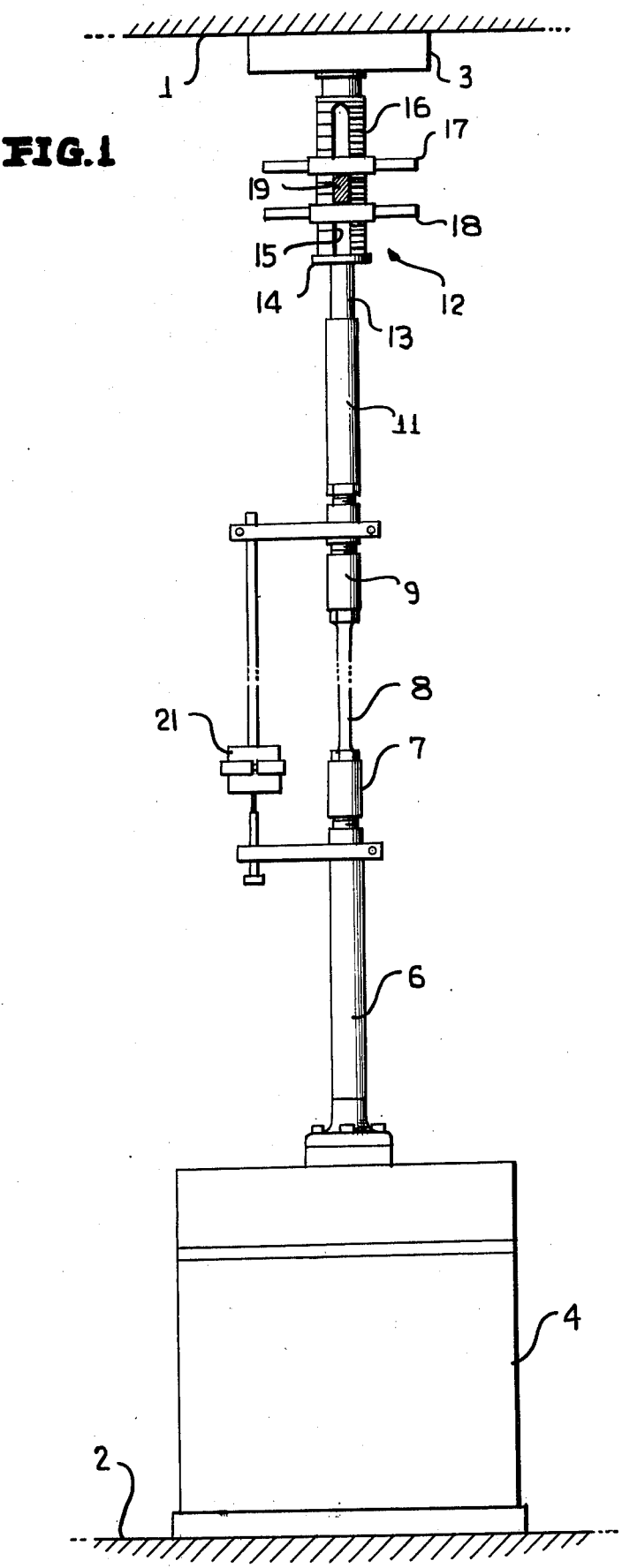
FIG. 1 is a view in elevation of the arrangement of the physical parts constituting the mechanical structure of the present invention.

Referring now to FIG. 1 of the accompanying drawing there is illustrated the mechanical details of the apparatus of the present invention. The apparatus comprises diagramatically illustrated upper and lower frame members 1 and 2, respectively, a load cell 3 secured to the upper frame member 1 and a voice coil, magnetic vibrator-linear motor 4 secured to the lower frame member 2. A lower connecting rod 6 extends from the active member of the voice coil motor to a lower specimen grip 7. A specimen or sample 8 is secured between the lower specimen grip 7 and an upper specimen grip 9 in turn connected to an upper connecting rod 11.

The upper connecting rod 11 is attached to a mechanism 12 adjustable to provide zero stress on the sample 8 prior to commencement of the tests.

Figure 2:
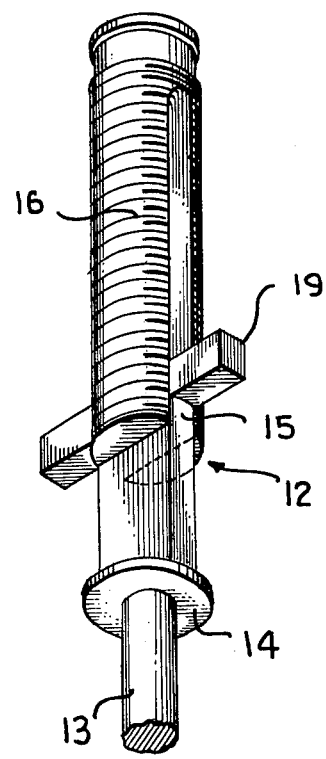
FIG. 2 is a perspective view of a mechanism for adjusting the apparatus for zero stress prior to commencement of testing.

Referring to FIG. 2 the mechanism 12 comprises a cylinder 13 terminating in a disc 14 to which is secured a T-bar 15 being of rectangular horizontal cross-section. The bar 15 is disposed in an externally-threaded vertically slotted cylinder 16 secured to the load cell 3. The diameter of the cylinder 16 is approximately equal to the maximum rectangular dimension of the T-bar.

Nuts 17 and 18 threadedly engage the cylinder 16 one above and one below cross-member 19 of the T-bar 15 whereby the position thereof may be adjusted after loading of the specimen 8 to take up the slack in the mechanism but maintain substantially zero stress.

A linear variable differential transformer 21 of conventional design is connected between the lower and upper connecting rods 6 and 11, respectively, to measure elongation of the sample.

In operation, by means to be described subsequently, the voice coil motor applies a force to the apparatus whereby the specimen is placed either in tension or compression depending upon the test to be conducted. The stress is measured by load cell 3 while elongation or compression is measured by the linear variable differential transformer 21.

During a creep test the load cell ideally measures stress but in fact measures load; stress varying to the extent that the cross-sectional area of the specimen changes under load. During a stress relaxation test the linear variable differential transformer (LVDT) 21 measures strain to the extent that constant displacement can be achieved by the circuitry in response to signals generated by the LVDT 21.

Referring specifically to FIG. 3, command signal employed for static tests (typically a step function) is amplified by amplifier 101 and then passed to a third order low-pass filter circuit 102. The purpose of filter 102, which is described in greater detail with respect to FIG. 4, is to: (1) delay the leading edge of the applied step signal so that it does not rise so fast as to produce overshoot in the servo loop which drives motor 4; and (2) permit the step signal which is applied to the servo loop to reach its final value as fast as possible without producing such overshoot. In other words, filter 102 is optimized for the particular mechanical system so that an underdamped, fast-responding loop can be employed.

The command signal employed for dynamic tests (typically, sine waves up to 250 Hz) is amplified by amplifier 103 and summed with the output signal from filter 102 at summing amplifier 104. The resulting command signal is applied to the positive input terminal of differential amplifier 105. The negative input terminal of differential amplifier 105 receives the loop feedback signal to be described below. The output signal from differential amplifier 105 is the loop error signal which is monitored by meter circuit 106 and passed through an adjustable lead/lag circuit 107. For example, circuit 107 may be an amplifier having a gain adjustable from $-1$ to $+1$, suitable for providing necessary lead/lag adjustment during stabilization of the servo loop. The signal is then integrated by loop integrator 108.

During the closed loop operational mode, the output signal from integrator 108 is passed through switch 110 in the C.L. position to amplifier 111 which in turn drives motor 4. In the open loop operational mode an external command signal is passed through amplifier 109, switch 110 in the O.L. position, and amplifier 111 to drive motor 4.

If a creep test is being performed, switch 114 is in the LOAD position, permitting the load (stress) signal from load cell 3 to be fed back to differential amplifier 105. Specifically, motor 4 applies a force to test sample 8 and the displacement in the sample is monitored by LVDT 21 which provides an electrical signal proportional to the displacement (i.e. creep). This signal is amplified by amplifier 112 and monitored at recorder/meter 115 as a measure of strain. The load signal from load cell 3 is amplified by amplifier 113 and passed through switch 114 to differential amplifier 105. The servo loop acts to null the error signal from differential amplifier 105 and thereby hold constant the force applied to sample 8 by motor 4. The relay contacts 139, 141 in series with LVDT 21 and amplifier 112 relates to the calibration interlock circuit described in greater detail below with reference to FIG. 5. For present purposes, it is assumed that these contacts are closed during the creep test described.

For a relaxation test, switch 114 is in the DISPL position, permitting the displacement (applied strain) signal from LVDT 21 to be fed back to differential amplifier 105. Specifically, motor 4 applies a variable force to test sample 8 such that the displacement of the sample remains constant. This force, or load, is monitored by load cell 3 which produces a proportional load signal. This load signal is amplified by amplifier 113 and monitored at recorder/meter 116 as a measure of load. The displacement signal is amplified by amplifier 112 and passed to differential amplifier 105 through switch 114 to hold the sample displacement constant. Again, it is assumed that contacts 139, 141 are closed during the relaxation test.

For the described static tests, during which a step function command signal is applied to the servo system, displacement or load is measured as a function of time in response to the applied step function. For such tests, recorder/meter circuits 115 and 116 include high speed recorders, digital data log recorders, or their equivalents, which provide a plot of the measured parameter against a time scale.

The servo loop is conventional for the type of system described. However, the use of filter circuit 102 to delay the static test command signal is novel in that the delay is optimized to the system constants. Specifically, considering the mass of the system parts, the stiffness of the test sample, and the time constant of the underdamped servo loop, the characteristic of filter 102 is chosen to permit the fastest possible rise time without causing overshoot. Placing the optimized filter outside the servo loop per se eliminates any effect on the intrinsic stability of the servo loop; in addition, it avoids additional damping and associated sluggishness of response in the servo loop. A particular filter circuit suitable for use as circuit 102 is illustrated in FIG. 4. Specifically, the circuit comprises three cascaded low pass filter stages wherein the first two stages are passive and the third stage is an active filter including operational amplifier A1. Resistors R1, R2 and R3 are connected in series between the circuit input terminal and the inverting input terminal of amplifier A1. A capacitor C1 is connected between ground and the junction of resistors R1 and R2; R1 and C1 comprise the first filter state. A capacitor C2 is connected between ground and the junction of resistors R2 and R3; C2 and R2 comprise the second filter stage. A feedback capacitor C3 is connected between the output terminal and inverting input terminal of operational amplifier A1. Resistors R4 and R5 are connected in series across Capacitor C3, and the junction between R4 and R5 is returned to ground through the series combination of resistor R6 and capacitor C4. The third filter stage includes components R3, R4, R5, R6, C3 and C4. Output impedance for the circuit is determined by resistor R7 and variable resistor R8.

The circuit of FIG. 4 is a third order low pass filter which suppresses the first two derivatives of the applied signal. The component values are selected to optimize the rise time of a step function to the system parameters. For a particular embodiment, in a system wherein the step response reached 99% of its final value within 20 milliseconds, the following component values were employed:

R1, R3 — 18.2 Kohms
R2 — 73.2 Kohms
R4, R5 — 54.9 Kohms
R6 — 300 ohms
C1, C2 — 0.22 uf
C3 — 0.022 uf
C4 — 0.1 uf Other component values and, for that matter, other circuit configurations may be employed. The important point is that the input step function be delayed only as much as necessary to prevent overshoot, considering the mechanical parameters of the system and the parameters of the underdamped servo loop.

Figure 5:
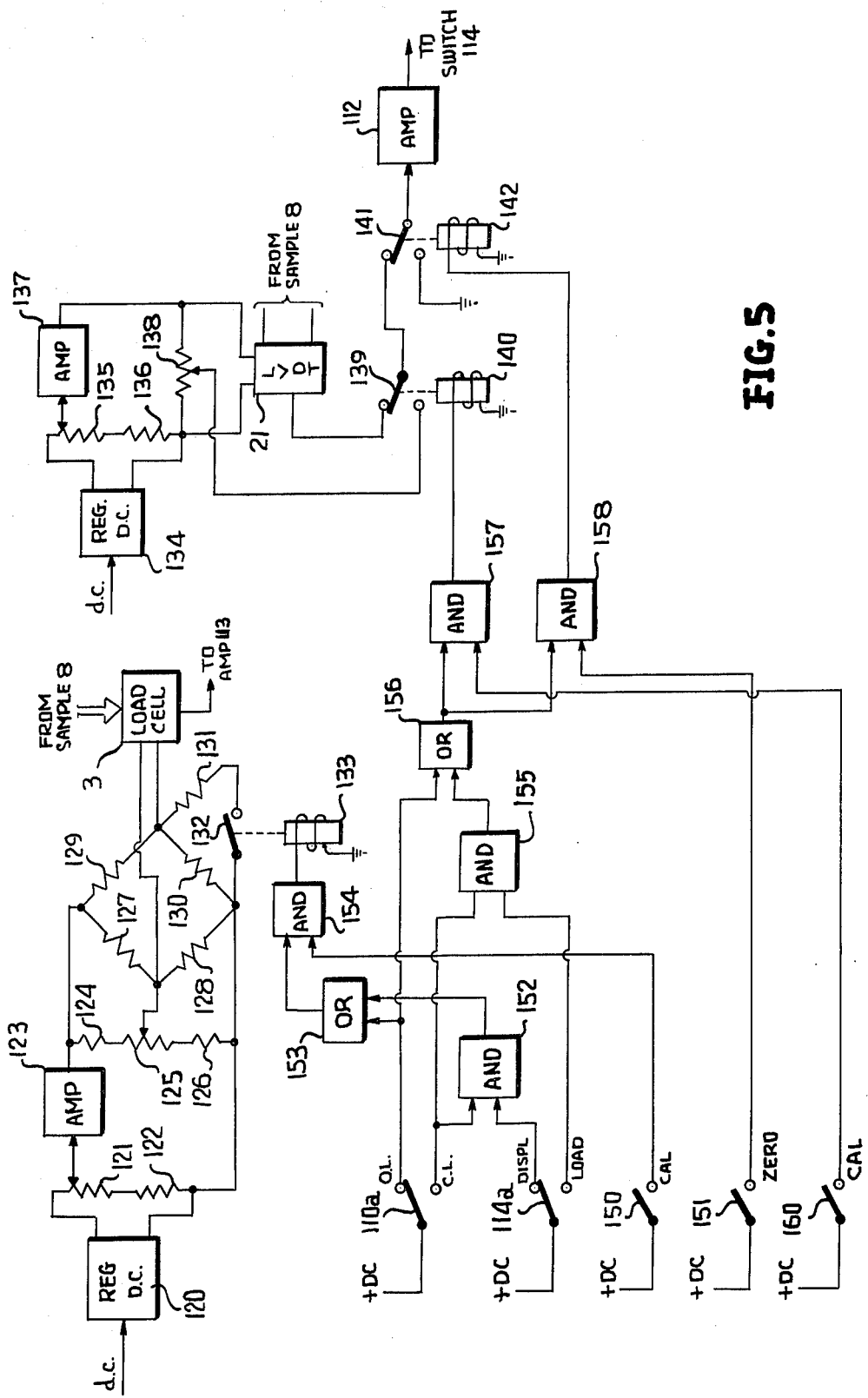
FIG. 5 is a logic diagram of the calibration interlock feature of the present invention.

Referring once again to FIG. 3, calibration of the load cell recorder/meter circuit 116 normally involves changing the distribution of electrical excitation across load cell 3. Calibration of recorder/meter circuit 115 involves switching a calibration signal into amplifier 112 in place of the signal from LVDT 21. In either case, if the parameter in question is being fed back to control loop operation, the change in signal level occasioned by introduction of the calibrate mode results in large transient conditions in the servo loop. Such transient conditions ruin any measurement in progress and could possibly cause damage to the motor and/or sample 8. The circuit of FIG. 5 is provided to prevent this from happening. Specifically, the excitation for load cell 3 includes a d.c. voltage regulator 120 across which are connected potentiometer 121 and resistor 122 in series. The wiper arm of potentiometer 121 applies the selected voltage level to amplifier 123 which applies the amplified level across the supply junctions of a load cell bridge comprising resistors 127, 128, 129, 130. Load cell 3 is a mechanical schematic representation of the load cell, shown connected across the output junctions of the bridge. A balance adjustment circuit includes resistor 124, potentiometer 125 and resistor 126 connected in series across the output of amplifier 123. The wiper arm of potentiometer 125 is connected to one of the bridge output junctions. A series circuit comprising calibration resistor 131 and relay contact 132 is connected between the other output junction and a supply junction of the bridge.

The load calibration circuit as thus far described is quite conventional. The normally balanced bridge is unbalanced during calibration by placing calibrate resistor 131 in parallel with load cell bridge resistor 130. This changes the excitation distribution across of the load cell 3 so that its output signal changes accordingly. If the load signal is controlling loop operation in the circuit of FIG. 3, the undesired effects described above come about. This is prevented according to the present invention by preventing closure of contact 132 unless certain logic conditions, described below, are met.

The excitation circuit for LVDT 21, which is similarly conventional, includes a d.c. regulator 134 across which are connected potentiometer 135 and resistor 136 in series. The wiper arm of potentiometer 135 delivers the selected d.c. level to amplifier 137 which supplies the LVDT excitation level across potentiometer 138. The wiper arm from the potentiometer supplies the displacement calibration signal. The displacement signal from LVDT 21 and the displacement calibration signal from potentiometer 138 are alternatively applied to displacement amplifier 112. It is readily seen that switching the displacement calibration level for the displacement signal level can adversely affect servo loop operation if the displacement signal is controlling loop operation. The logic circuits described below preclude this condition.

Before describing the logic circuit and conditions, it is to be understood that, to facilitate understanding, the logic has been represented in as simple a convention as possible without regard for savings of cost, space, or energy dissipation. Therefore, manually-actuated switches, relays, and AND and OR gates have been employed in the FIG. 5 representation. In an actual embodiment, equivalent integrated circuitry employing equivalent electronic switching and NAND/NOR logic can be employed. In fact, any functionally equivalent switching and logic components may be utilized to achieve the results obtained in the FIG. 5 circuit.

Switch 110a is, in effect, a second pole of switch 110 of FIG. 3. Specifically, switch 110a has an open loop (O.L.) position and a closed loop (C.L.) position. A binary one or +d.c. level is applied to either output line, depending upon the switch position. Similarly, switch 114a is, in effect, a second pole of switch 114 of FIG. 3. Switch 114a applies a binary one or +d.c. level to either its DISPL or LOAD terminals, depending upon the switch position. A load calibrate switch 150 and a displacement calibrate switch 160 provide a binary one level when closed, and a zero switch 151 provides a binary one level when closed. All five switches are positioned under control of the system operator.

A two-input AND gate 152 receives the C.L. and DISPL signals and feeds a two-input OR gate 153 which also receives the O.L. signal. The output from OR gate 153 feeds two-input AND gate 154 along with the CAL signal from switch 150. The output signal from AND gate 154 controls relay 133 which has normally-open contact 132 in series with the calibrate resistor 131 in the load cell bridge circuit.

Load calibration requires actuation of relay 133 so that contact 132 is closed. Relay 133 can be actuated only for one of the following sets of conditions:

(1) Calibrate switch 150 is closed and the servo loop is open. Under these conditions the O.L. signal from switch 110a enables OR gate 153 which in turn enables AND gate 153 along with the CAL signal to actuate relay 133; or (2) Calibrate switch 150 is closed, the servo loop is operating closed loop, and the displacement signal from LVDT 21, rather than the load signal from load cell 3, is controlling loop operation. Under such conditions, the binary one level at the DISPL terminal of switch 114a and the C.L. signal from switch 110a enable AND gate 152 which enables OR gate 153. The latter, together with the CAL signal, enables AND gate 154 to actuate relay 133. During closed loop operation, if the load signal is controlling loop operation, switch 114a is in the LOAD position and prevents calibration of the load signal circuitry.

Additional logic circuitry for controlling displacement calibration includes a two-input AND gate 155 which is enabled when switch 110a is in the C.L. (closed loop) position and switch 114a is in the LOAD position. The output signal from AND gate 155 is fed to two-input OR gate 156 along with the signal from the O.L. (open loop) terminal of switch 110a. The output signal from OR gate 156 serves as an input signal to each of two-input AND gates 157 and 158. The other input signal for AND gate 157 is the CAL signal from calibrate switch 160; the other input signal for AND gate 158 is the ZERO signal from zero switch 151. AND gate 157 in turn controls actuation of relay 140 which has a set of contacts 139. AND gate 158 controls actuation of relay 142 which has a set of contacts 141. In the normally closed position of contacts 139 and 141, the displacement signal from LVDT 21 is passed to amplifier 112. If either of relays 140, 142 is actuated, this path is broken. Actuation of relay 140 applies the displacement calibration signal to amplifier 112. Actuation of relay 142 grounds the input to amplifier 112 so that the circuitry may be zeroed.

Actuation of relay 140 to effect displacement calibration can result only from one of the following sets of conditions:

(1) Calibrate switch 160 is closed and the servo is operating open loop. Under these conditions switch 110a is in the O.L. position to enable OR gate 156 which enables AND gate 157 along with the closed calibrate switch 160

(2) Calibrate switch 160 is closed, the servo loop is closed, and the load signal, rather than the displacement signal, is controlling loop operation. Under these conditions AND gate 155, OR gate 156 and AND gate 157 are enabled.

Actuation of relay 142 for a zeroing operation requires the same conditions as actuation of relay 140 except that zero switch 151 must be closed rather than calibrate switch 160, and AND gate 158 is enabled rather than AND gate 157.

The d.c. or voice coil motor employed in the present invention may be any type of motor having a broad range of response from d.c. to middle range audio frequencies. Such a motor may be any one of many different types of motors of which the voice coil motor is one. Such motors are identified in many ways such as shake motors, vibrator motors, d.c. motors, voice coil motors, etc., and are all well known in the art. Such motors have been used in the prior art to conduct dynamic tests on materials but due to the rapid response characteristics of such motors and the slow response of mechanical testing devices have not been utilized in transient tests.

While I have described and illustrated one specific embodiment of my invention, it will be clear that variations of the details of construction which are specifically illustrated and described may be resorted to without departing from the true spirit and scope of the invention as defined in the appended claims.

I claim:

1. Apparatus for conducting transient characterization tests on specimens of materials to be tested comprising means for securing a specimen under a no load condition, an electrically actuable direct current voice coil shaker motor secured to one end of said means whereby to apply a force rapidly to a specimen, command means for selectively applying an electrical step function actuation signal to said shaker motor, means for producing an electrical response signal indicative of a predetermined parameter related to the force applied to the specimen, a motor control circuit responsive to said response signal for maintaining said parameter at a specified magnitude, said motor control circuit producing a d.c. signal directly coupled to said motor.

2. Apparatus for conducting transient characterization tests on specimens of materials to be tested comprising means for securing a specimen under a no load condition, an electrically actuable direct current voice coil shaker motor secured to one end of said means whereby to apply a force rapidly to a specimen, command means for selectively applying an electrical step function actuation signal to said shaker motor, means for producing an electrical response signal indicative of a predetermined parameter related to the force applied to the specimen, a motor control circuit responsive to said response signal for maintaining said parameter at a specified magnitude, and an input circuit disposed between said means for producing and said motor control circuit having a time constant which delays application of said actuation signal to said shaker motor by the minimum amount of time necessary to prevent overshoot in said apparatus.

3. The method of conducting closed loop transient tests on a specimen of material to be tested comprising the steps of applying a d.c. control signal to a d.c. shaker motor, transmitting the motion of the shaker motor to the specimen whereby to transmit force thereto, producing an electrical step function command signal, producing an electrical response signal related to the force applied to the specimen, and coupling said command and response signals to a motor control circuit whereby to produce said d.c. control signal.

4. The method according to claim 3 further comprising the step of delaying said step-function command signal the minimal amount of time necessary to prevent overshoot in said closed loop.

5. In a materials testing device of the type in which a motor is actuated to apply a load to a sample under test, a motor control arrangement suitable for responding to a step function command signal, said control arrangement being characterized by:

an underdamped servo loop responsive to command signals applied thereto for controlling said motor; and a command signal shaping circuit for delaying the leading edge of said step function command signal before it is applied to said servo loop, said delay being only long enough to prevent overshoot in said loop.

6. A materials testing device for applying force to a sample under test and monitoring the effects of said force on said sample, comprising:
an underdamped servo loop, including
grip means for holding said sample;
a controlled motor for applying said force to said sample through said grip means;
control means for controlling the force applied by said motor in response to an externally supplied command signal;
load monitoring means for providing an electrical load signal proportional in amplitude to the force applied to said sample by said motor;
strain monitoring means for providing an electrical displacement signal proportional in amplitude to the displacement produced in said sample by the applied motor force;
means for alternatively feeding said load and displacement signals back to said control means to alternatively maintain the applied motor force and the sample displacement, respectively, constant;
wherein said externally supplied command signal is a step function, and further comprising a signal shaping circuit for delaying said command signal before it is applied to said control means such that the leading edge of said step function is applied to said control means with as fast a rise time as possible short of producing overshoot in said servo loop.

7. A materials testing device for applying force to a sample under test and monitoring the effects of said force on said sample, comprising:
grip means for holding said sample;
a controlled motor for applying said force to said sample through said grip means;
control means for controlling the force applied by said motor in response to an externally supplied command signal;
load monitoring means for providing an electrical load signal proportional in amplitude to the force applied to said sample by said motor;
strain monitoring means for providing an electrical displacement signal proportional in amplitude to the displacement produced in said sample by the applied motor force;
means for alternatively feeding said load and displacement signals back to said control means to alternatively maintain the applied motor force and the sample displacement, respectively, constant;
displacement calibration means including means for applying a displacement calibration signal to said device in place of said displacement signal; and
logic means for inhibiting application of said displacement calibration signal to said device in place of said displacement signal when said displacement signal is being fed back to said control means.

8. The device according to claim 7 further comprising:
load calibration means including means for exciting said load monitoring means to provide a known output amplitude; and
further logic means for inhibiting said load calibration means when said load signal is being fed back to said control means.

9. The device according to claim 8 wherein said externally supplied command signal is a step function and wherein said motor is a voice coil motor.

10. A materials testing device for applying force to a sample under test and monitoring the effects of said force on said sample, comprising:
grip means for holding said sample;
a controlled motor for applying said force to said sample through said grip means;
control means for controlling the force applied by said motor in response to an externally supplied command signal;
load monitoring means for providing an electrical load signal proportional in amplitude to the force applied to said sample by said motor;
strain monitoring means for providing an electrical displacement signal proportional in amplitude to the displacement produced in said sample by the applied motor force;
means for alternatively feeding said load and displacement signals back to said control means to alternatively maintain the applied motor force and the sample displacement, respectively, constant;
wherein said externally supplied command signal is a step function and wherein said motor is a voice coil motor.

11. In a materials testing device of the type wherein a servo loop controls a motor in response to applied command signals and the motor applies a load to deform a sample under test, said device having a first operational mode wherein the applied load is maintained constant by said servo loop and the resulting sample displacement is measured, and a second operational mode whereby the sample displacement is held constant by said servo loop and the load required therefor is measured, said device being characterized by:
first operable-actuable means for calibrating sample displacement measurements;
second operator-actuable means for calibrating applied load measurements;
first interlock means for automatically inhibiting said first operator-actuable means during said second operational mode; and
second interlock means for automatically inhibiting said second operator-actuable means during said first operational mode.

12. The device according to claim 11 wherein said servo loop can be opened to permit open loop measurements of sample displacement and applied load, said device being further characterized by logic means for over-riding said first and second interlock means during said open loop measurements to prevent inhibition of said first and second operator-actuable means.

* * * * *